(12) United States Patent
Lu et al.

(10) Patent No.: US 8,846,316 B2
(45) Date of Patent: Sep. 30, 2014

(54) BIOMARKER FOR HUMAN LIVER CANCER

(71) Applicant: Industrial Technology Research Institute, Hsinchu (TW)

(72) Inventors: Chang-Yi Lu, New Taipei (TW); Meng-Tsung Tien, Chaozhou Township, Pingtung County (TW); Cheng-Tao Wu, New Taipei (TW); Yih-Huei Uen, Tainan (TW); Kai-Yuan Lin, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/685,551

(22) Filed: Nov. 26, 2012

(65) Prior Publication Data

US 2013/0288239 A1 Oct. 31, 2013

Related U.S. Application Data

(60) Provisional application No. 61/640,512, filed on Apr. 30, 2012.

(51) Int. Cl.
| | | |
|---|---|---|
| C12Q 1/68 | (2006.01) | |
| C12P 19/34 | (2006.01) | |
| C07H 21/02 | (2006.01) | |

(52) U.S. Cl.
CPC ........ C12Q 1/6886 (2013.01); *C12Q 2600/158* (2013.01); *C12Q 2600/178* (2013.01); *C12Q 2600/154* (2013.01)
USPC .......... 435/6.1; 435/91.2; 536/23.1; 536/24.3

(58) Field of Classification Search
None
See application file for complete search history.

(56) References Cited

U.S. PATENT DOCUMENTS

| 2006/0105360 A1 | 5/2006 | Croce et al. |
|---|---|---|
| 2010/0197770 A1 | 8/2010 | Wang et al. |
| 2011/0223607 A1 | 9/2011 | Qu et al. |

FOREIGN PATENT DOCUMENTS

| CN | 102080082 | 6/2011 |
|---|---|---|
| CN | 102149827 A | 8/2011 |
| EP | 2336353 | 6/2011 |
| EP | 2341145 | 7/2011 |
| EP | 2354246 | 8/2011 |
| TW | 200912002 | 3/2009 |
| TW | 201118178 | 6/2011 |
| WO | WO-2008/054828 A2 | 5/2008 |
| WO | WO 2009132273 | 10/2009 |
| WO | WO 2009137807 | 11/2009 |
| WO | WO 2009153775 | 12/2009 |
| WO | WO 2010042831 | 4/2010 |
| WO | WO 2010062706 | 6/2010 |
| WO | WO 2010098862 | 9/2010 |
| WO | WO 2010126370 | 11/2010 |

OTHER PUBLICATIONS

Costello J.F. et al. Jun. 24, 1994 The Journal of Biological Chemistry, 269, 17228-17237.*
Brabender J. et al. Clin Cancer Res 2003;9:223-227.*
Juppner H. Bone vol. 17, No. 2, Supplement, Aug. 1995:39S-42S.*
Hao M. et al. Journal of Hepatology vol. 54Supplement 1, p. S393.*
Xuedan Chen et al., "CpG island methylation status of miRNAs in esophageal squamous cell carcinoma", Int. J. Cancer: 130, 2012, pp. 1607-1613.
Yi-Wen Huang et al., "Epigenetic Repression of *microRNA-129-2* Leads to Overexpression of *SOX4* Oncogene in Endometrial Cancer", *Cancer Res* 2009;69:pp. 9038-9046. Published Online First Nov. 3, 2009.
Ruizhe Shen et al., "Epigenetic repression of microRNA-129-2 leads to overexpression of SOX4 in gastric cancer", Biochemical and Biophysical Research Communications 394 (2010) pp. 1047-1052.
Eva Bandres et al., "Epigenetic regulation of microRNA expression in colorectal cancer", Int. J. Cancer: 125, pp. 2737-2743 (2009).
Jharna Datta et al., "Methylation Mediated Silencing of MicroRNA-1 Gene and Its Role in Hepatocellular Carcinogenesis", *Cancer Res* 2008;68: pp. 5049-5058, Published online Jul. 1, 2008.
Mayuko Furuta et al., "miR-124 and miR-203 are epigenetically silenced tumor-suppressive microRNAs in hepatocellular carcinoma", Carcinogenesis vol. 31 No. 5 pp. 766-776, 2010.
Jinfeng Huang et al., "Down-Regulated MicroRNA-152 Induces Aberrant DNA Methylation in Hepatitis B Virus—Related Hepatocellular Carcinoma by Targeting DNA Methyltransferase 1", Hepatology, vol. 52, No. 1, 2010, pp. 60-70.
Hiromu Suzuki et al."Methylation-associated silencing of microRNA-34b/c in gastric cancer and its involvement in an epigenetic field defect", Carcinogenesis vol. 31 No. 12 pp. 2066-2073, 2010.
Minoru Toyota et al.,"Epigenetic Silencing of *MicroRNA-34b/c* and *B-Cell Translocation Gene 4* is Associated with CpG Island Methylation in Colorectal Cancer", *Cancer Res* 2008;68:pp. 4123-4132. Published online Jun. 2, 2008.
Jin Hou et al., "Identification of miRNomes in Human Liver and Hepatocellular Carcinoma Reveals miR-199a/b-3p as Therapeutic Target for Hepatocellular Carcinoma", Cancer Cell 19, 232-243, Feb. 15, 2011.
Office Action issued in corresponding TW Application 101149687 mailed Apr. 23, 2014.

* cited by examiner

*Primary Examiner* — Stephen Kapushoc
(74) *Attorney, Agent, or Firm* — Muncy, Geissler, Olds & Lowe, P.C.

(57) ABSTRACT

The disclosure relates to a method for determining incidence of liver cancer in a subject, including detecting methylation level or expression level of one microRNA miR-129-2 in a bio-sample from the subject. In the case that the methylation level of the microRNA in the bio-sample is higher or the expression level of the microRNA in the bio-sample is lower relative to that of the corresponding microRNA in a control sample, indicates that the subject is predisposed to or afflicted with liver cancer.

4 Claims, 20 Drawing Sheets

BIOMARKER FOR HUMAN LIVER CANCER

CROSS REFERENCE TO RELATED APPLICATIONS

This application claims the benefit of U.S. Provisional Application No. 61/640,512, filed Apr. 30, 2012, which is incorporated herein by reference.

INCORPORATION BY REFERENCE OF SEQUENCE LISTING

A sequence listing submitted as a text file via EFS-Web is incorporated herein by reference. The text file containing the sequence listing is named "0965-A23943-US_Seq_Listing.txt"; its date of creation is Nov. 21, 2012; and its size is 2,100 bytes.

BACKGROUND

1. Technical Field

The technical field relates to a biomarker for human liver cancer.

2. Background

MicroRNAs (miRNAs) are an abundant class of short endogenous RNAs with approximately 22 nucleotides. MiRNAs act as post-transcriptional regulators of gene expression by base-pairing with their target mRNAs, resulting in the degradation of target mRNA or inhibition of the target mRNA expression.

Several studies show that the expression of miRNAs is aberrant in cancer cells. Genome-wide studies also reveal that miRNAs are present in chromosome regions exhibiting cancer-related loss of heterozygosity. In several cancer cell lines, the expression of miRNAs has been observed to be suppressed. It is suggested that miRNAs suppress tumor formation through inhibiting the oncogene expression and modulating genes involved in cell apoptosis or differentiation. The miRNAs functioning like tumor suppressor genes are also named "tumor suppressor miRNA". It has been reported that for 68% of chronic lymphocytic leukemia (CLL) patients having deleted or suppressed miR-15 and miR-16; miR-143 and miR-145 showed lower expression levels in colon and lung cancer tissues than corresponding normal tissues; and miRNA let-7 was suppressed in lung cancer cells and a poor prognosis of lung cancer may be detected by down regulation of miRNA let-7.

Studies have shown that DNA methylation plays a role in tumor suppressor miRNAs modulation. DNA methylation refers to the conversion of cytosine to 5-methylcytosine in CpG dinucleotides by DNA methyltransferase. CpG dinucleotides are commonly rich at 5'-terminal regions, also termed "CpG sites". Studies show that, in about 70% of human genes, CpG sites can be found in promoter regions. As CpG sites in promoter regions are hypermethylated, it has been suggested that the encoded genes in the down stream may be inhibited to precede transcription and therefore the genes are not expressed. Thus, it has been suggested that hypermethylated CpG sites can be recognized by some methyl binding proteins accompanied with histone deacetylase (HDAC) and co-repressor so as to change chromosomal structures and form inactive heterochromatins. Several studies show that aberrant DNA methylation occurs in early cancer stages, which may cause tumor suppressor genes not expressed. Recent studies show that DNA methylation not only inhibits tumor suppressor gene expression but also decreases tumor suppressor miRNA expression.

SUMMARY

The embodiments of present disclosure discloses a microRNA and its methylation used as a biomarker for detecting and diagnosing liver cancer.

One embodiment of the present disclosure provides a method for determining incidence of liver cancer in a subject, comprising detecting methylation level of miR-129-2 in a bio-sample from the subject, wherein the methylation level is detected by a method selected from the group consisting of a combined bisulfite restriction analysis (COBRA), quantitative methylation-specific polymerase chain reaction (q-MSP) bisulfite sequencing, pyrosequencing, next generation sequencing (NGS), or methylation array, and wherein the methylation level of the microRNA in the bio-sample is higher relative to the methylation level of the corresponding microRNA in a control sample, indicating that the subject is predisposed to or afflicted with liver cancer.

Another embodiment of the present disclosure provides a method for determining incidence of liver cancer in a subject with a quantitative reverse transcription polymerase chain reaction (qRT-PCR) or miRNA array, comprising detecting the expression level of miR-129-2 in a bio-sample from the subject, wherein the expression level of microRNA in the bio-sample is lower relative to the expression level of the corresponding microRNA(s) in a control sample, indicating that the subject is predisposed to or afflicted with liver cancer.

DRAWINGS

The present disclosure can be more fully understood by reading the subsequent detailed description and examples with references made to the accompanying drawings, wherein:

FIG. 1 shows methylation of miR-129-2 in normal liver tissues, a normal liver cell (HH) and six HCC cells by COBRA analysis according to the embodiment;

FIG. 2A~2F show methylation percentages of miR-129-2 in normal liver tissues, a normal liver cell (HH) and six HCC cells by bisulfite sequencing according to the embodiment;

DETAILED DESCRIPTION

Figure 1:
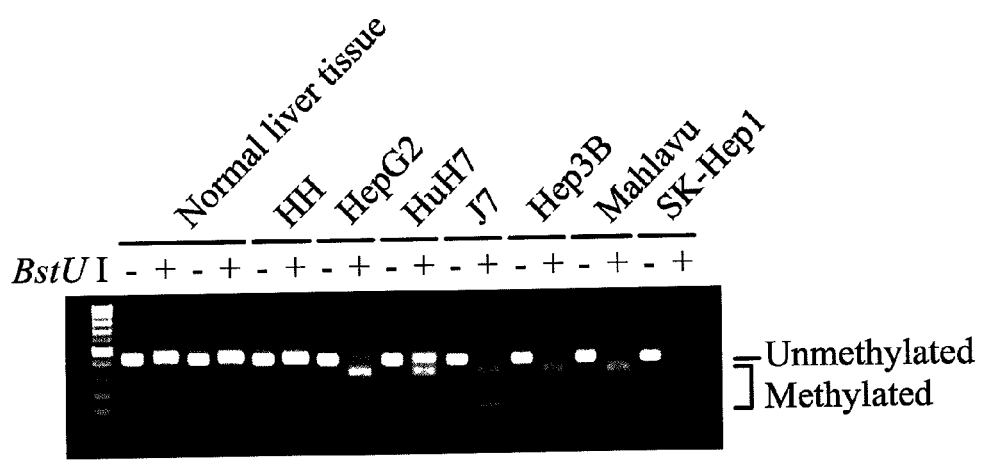

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The embodiment of present disclosure provides a novel microRNA (miRNA) as a biomarker for detecting human liver cancer. Based on a high-throughput CpG microarray platform, the inventors screened a plurality of miRNAs methylated in hepatocellular carcinoma (HCC) cells to find out one potential microRNA, miR-129-2, for the detection of liver cancer.

miRNA described herein refers to human (*Homo sapiens*) microRNAs, available in miRBases database (http://mirbase.org) or NCBI database (http://www.ncbi.nlm.nih.gov/). miRNA may comprise a stem-loop precursor form and a cleaved and processed mature form to generate two active fragments with 5'-terminal (namely "5p") and 3'-terminal (namely "3p"). According to the present disclosure, the microRNA, miR-129-2, is in precursor form with about 100 bp linear sequence as set forth in SEQ ID NOs. 1.

A subject predisposed to or suffering liver cancer can be determined according to the methylation level or status of the miRNA in the biosample from the subject relatively higher than that of corresponding miRNA in a control sample. The biosample for detection may be obtained from fresh or frozen liver cancer tissues, cells, bloods, serum or plasma, but not limited thereto. The control sample may be derived from a normal tissue, cell, blood, serum or plasma that is the same tissue type from a healthy person with disease free under diagnoses or from a normal tissue that is the same tissue type adjacent to which the tumor was formed.

The methylation status of miRNAs can be determined by combined bisulfite restriction analysis (COBRA), quantitative methylation-specific polymerase chain reaction (q-MSP) and bisulfite sequencing bisulfite sequencing, pyrosequencing, next generation sequencing (NGS) or methylation array. COBRA refers to an analysis for interrogating DNA methylation via restriction enzyme analysis of PCR-amplified bisulfite treated DNAs. The details of COBRA protocol can be found in DNA Methylation Protocols, Methods in Molecular Biology™, HUMANA Press, Totowa, N.J., vol. 200, p. 71-86.

The primer-pair for COBRA analyses of miR-129-2 comprises the nucleotide sequences as set forth in SEQ ID NOs: 4 and 5. However, the primers for miRNAs methylation analyses by using COBRA are not limited thereto. A person skilled in the art according to the present disclosure is able to design appropriate primer pairs for COBRA analyses of the miRNAs and thus, the primers suitable for COBRA analyses of the miRNAs are also included in the invention.

The methylation profile of the seven miRNAs may further be analyzed by bisulfite sequencing and quantitative methylation specific PCR (q-MSP). When treated with sodium bisulfite, cytosine (C) in DNA sequences is converted to uracil (U), but leave 5-methylcytosines (mC) unaffected. Thus, bisulfite treatment introduces specific changes in the DNA sequence and exhibits the information about the methylation status. In one example of the invention, the primer-pair for miR-129-2 in q-MSP may comprise the nucleotide sequences as set forth in SEQ ID NOs: 8 and 9, but not limited thereto. For the detail of bisulfite sequencing protocol, it can be found in DNA Methylation Protocols, Methods in Molecular Biology™, HUMANA Press, Totowa, N.J., vol. 200, p. 143-154.

In addition, one embodiment of the invention provides a method for determining incidence of liver cancer in a subject, comprising detecting the expression level of microRNA miR-129-2, in a bio-sample from the subject, wherein the expression level of the microRNA(s) in the bio-sample is lower relative to the expression level of the corresponding microRNA(s) in a control sample, indicating that the subject is predisposed to or afflicted with liver cancer The expression level of the miRNA may be determined by quantitative real time PCR (qRT-PCR) or miRNA array. QRT-PCR is a modified PCR characterized in that the amplified DNA is detected as the reaction progresses in real time. For qRT-PCR, the cycle at which fluorescence is detectable during the exponential phase is termed cycle threshold (Ct). The Ct value or delta Ct value ($\Delta$Ct) compared to reference genes can be used for the targeted DNA quantitation. In one example of the invention, the primer-pair for miR-129-2 in qRT-PCR may comprise the nucleotide sequences as set forth in SEQ ID NOs: 6 and 7, but not limited thereto. The down-regulated expression level of the miRNAs is corresponding to the methylation status of the miRNAs in human liver cancer, indicating that the miRNAs are reliable biomarkers for detection of liver cancer.

The microRNAs function in liver cancer is further determined by using colony formation. In one example, the microRNA(s) may be inserted to viral nucleic acids and entered to HCC cells through viral infection. The miRNAs functions in HCC cells would be revealed on the colony numbers of cells, showing that the miRNAs function as tumor suppressor genes in human liver cancer.

EXAMPLES

Materials and Methods

Patient Samples, Cell Culture and 5-Aza-Cytidine (5-AzaC) Treatment

Hepatoma cell lines, HepG2, HuH7, J7, Hep3B, Mahlavu and SK-Hep-1 were maintained in Dulbecco's modified Eagle's medium at 37° C. in a humidified, 5% $CO_2$ incubator. Twenty-four hours prior to treatment, HuH7 cells ($1 \times 10^5$ cells/well) and other hepatoma cells ($3 \times 10^5$ cells/well) were seeded into 6-well plates. Cells were treated with 5 μM 5-azaC (Sigma) for 3 days. Culture medium was replaced every 24 hours with fresh media containing 5-azaC. Forty-two paired HCC clinical samples comprising tumor and adjacent normal tissue, forty-one plasma samples, eight cirrhotic plasma and ten healthy were obtained from Chi Mei medical center, Tainan, Taiwan. Normal adult liver genomic DNA (control) for bisulfite sequencing and Methylation-specific PCR (MSP) were purchased from US Biological. CpGenome Universal Methylated DNA was purchased from Chemicon as MSP positive control.

Combined Bisulfite Restriction Analysis (COBRA) and Bisulfite Sequencing

Genomic DNA (1 µg) from HCC clinical samples, hepatoma cells and adult normal liver was bisulfite-converted using the EZ DNA methylation kit (Zymo Research) and used for PCR amplification. For COBRA, the PCR products were digested with the methylation-sensitive endonuclease BstUI at 60° C. overnight. Digested DNA fragments were visualized on 1.5% (w/v) ethidium bromide-stained agarose gels. The PCR products for bisulfite sequencing were cloned into pJET1.2/blunt cloning vector using CloneJET PCR cloning kit (Thermo Fisher Scientific). After transformation of Escherichia coli, approximate 10 clones were selected and sequenced using the ABI sequencing system (Applied Biosystems).

Real-Time Quantitative Methylation Analysis

Bisulfite converted DNA as previous described was amplified by fluorescence-based real-time methylation-specific PCR (qMSP) using SYBR green. Each reaction consisted of 1×PCR buffer, 0.25 mM dNTP, 0.25 µM forward primer and reverse primer each, 1.5 U FastStart Taq DNA polymerase (Roche) and 1 µl SYBR green (Cambrex) 1000× dilution in a total volume of 20 µl. Amplification was carried out on the ABI Prism 7000 sequence detection System under the following thermocycling conditions: 94° C. for 7 minutes, followed by 40 cycles of 94° C. for 30 seconds, 62° C. for 30 seconds and 72° C. for 30 seconds. According to previous description, methylation level was calculated by the difference of Ct values between β-actin and miR-129-2 as the following formula: $2^{[Ct(\beta\text{-}actin)-Ct(miR\text{-}129\text{-}2)]} \times 100$ for tissue samples or $2^{[Ct(\beta\text{-}actin)-Ct(miR\text{-}129\text{-}2)]} \times 1000$ for plasma samples.

Real-Time Quantitative Reverse Transcription Polymerase Chain Reaction (qRT-PCR)

Total RNA of hepatoma cells and HCC clinical samples was extracted using TRIzol reagent (Invitrogen). cDNA synthesis was performed with Superscript III reverse transcriptase according to the manufacturer's instructions (Invitrogen). Real-time quantitative polymerase chain reaction was performed on the ABI Prism 7000 sequence detection System using the SYBR Green PCR master mix (Applied Biosystems). For analysis of mature miRNA expression, TaqMan miRNA assay system (Applied Biosystems) was used as the manufacturer's manual. The relative expression level was analyzed by the ΔΔCt method, and U6 and RNU44 were used as an internal control.

Colony Formation

HuH7 and J7 cells were seeded at a density of $2\times10^4$ cells/well on 96-well plates. Cells were infected with recombinant lentivirus harboring miR-129-2 precursor or the control lentivirus according to the manufacturer's instructions. After twenty-four hours infection, cells were mixed with 0.7% top agar and transferred to a well containing 1% bottom agar in 6-well plates. The transfectants were selected using puromycin 5 µg/ml for four weeks. Colonies were washed with PBS, fixed with absolute methanol, and stained with a crystal violet solution (0.5%) for 1 hour.

Example 1

Identification of Potential miRNAs Regulated by DNA Methylation

The methylation status of miR-129-2 was determined in normal liver tissue and cell (HH) and six HCC cells (HepG2, HuH7, J7, Hep3B, Mahlavu and SK-Hep 1) according to COBRA. The result shown in FIG. 1 revealed that miR-129-2 was methylated in six HCC cells but unmethylated in normal liver tissue and cell.

Figure 2A:
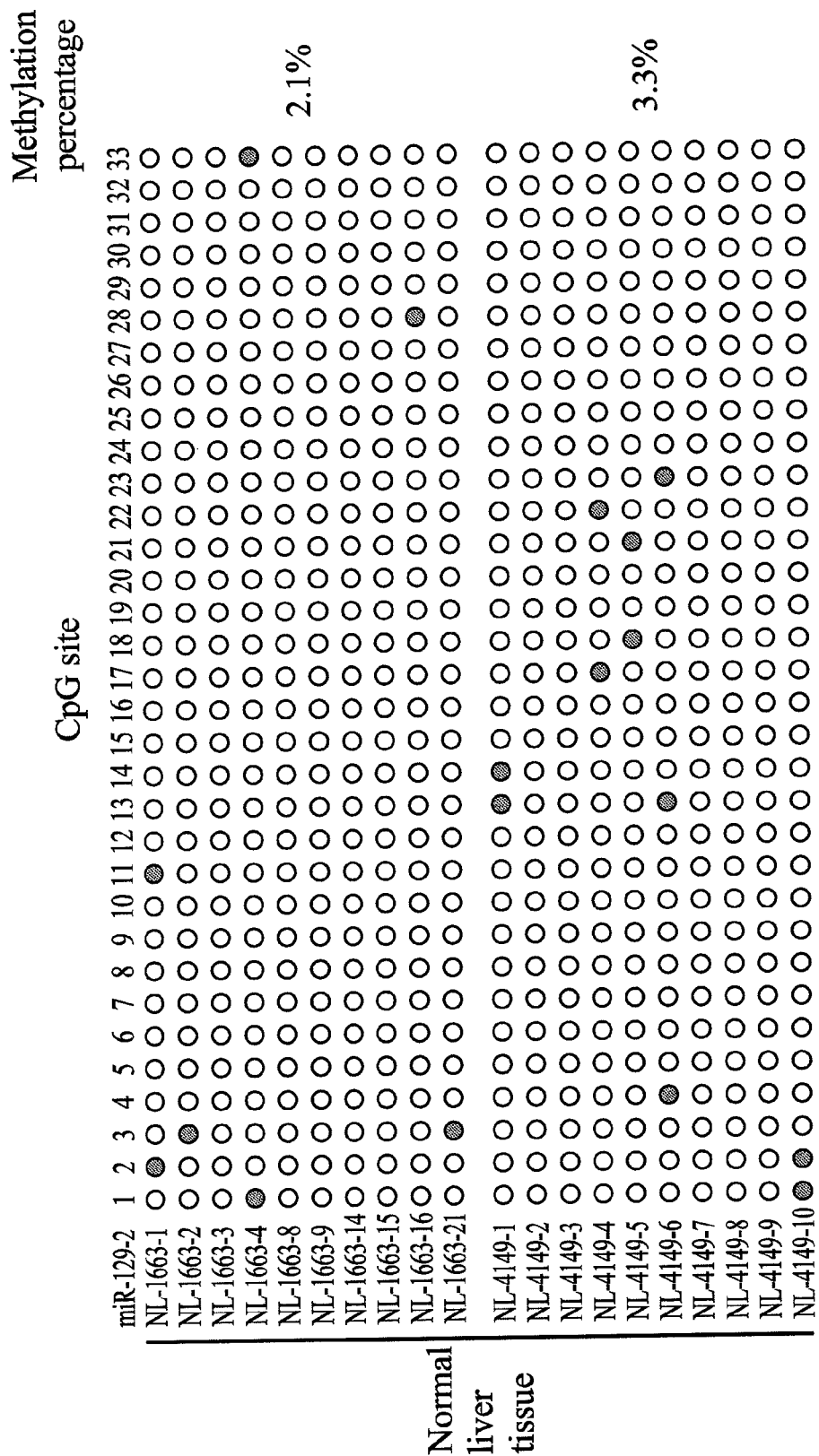
Figure 2B:
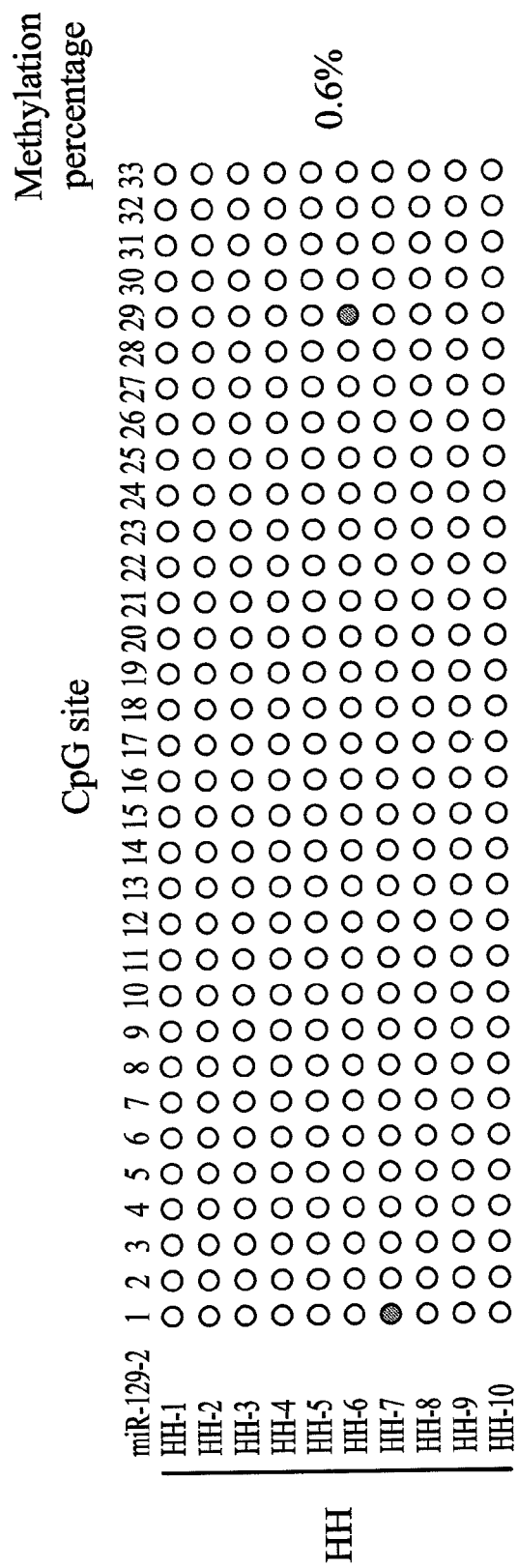
Figure 2C:
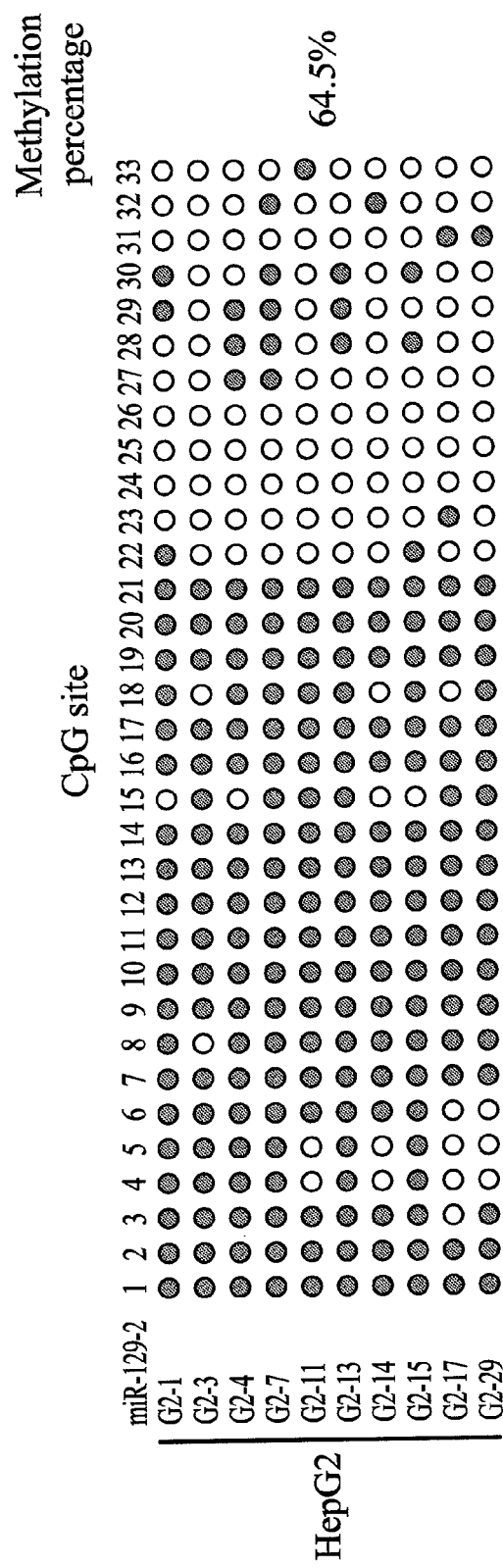
Figure 2D:
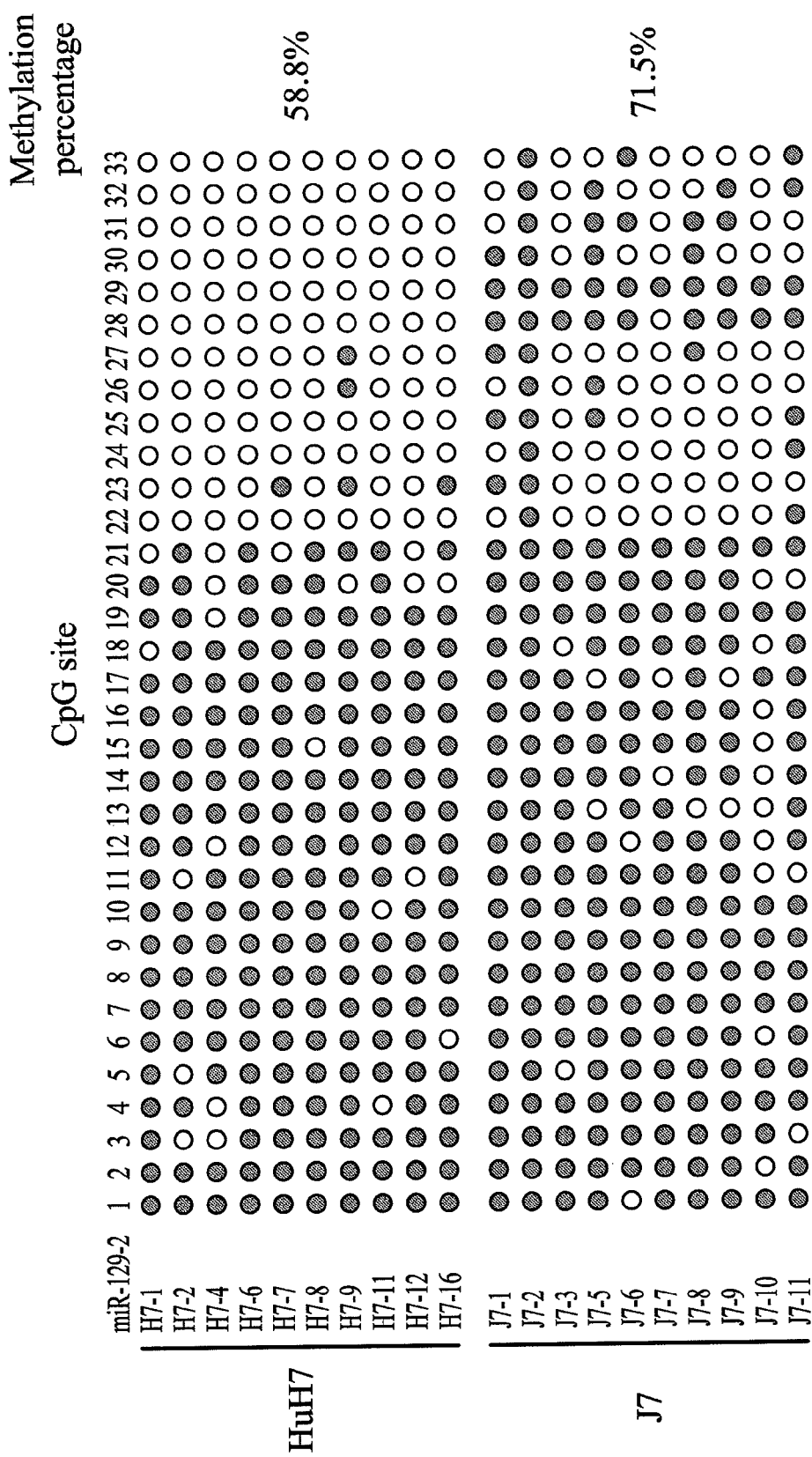
Figure 2E:
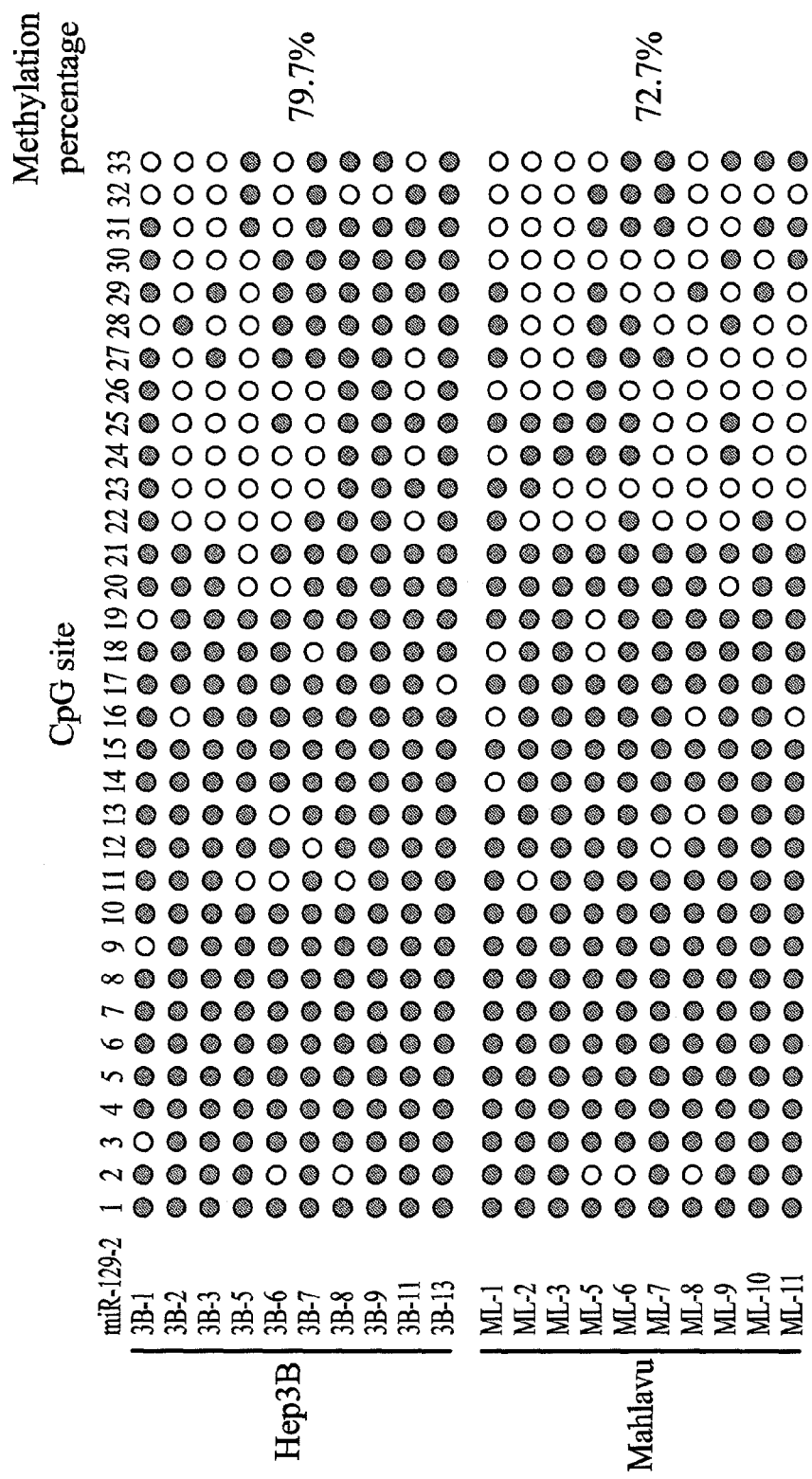
Figure 2F:
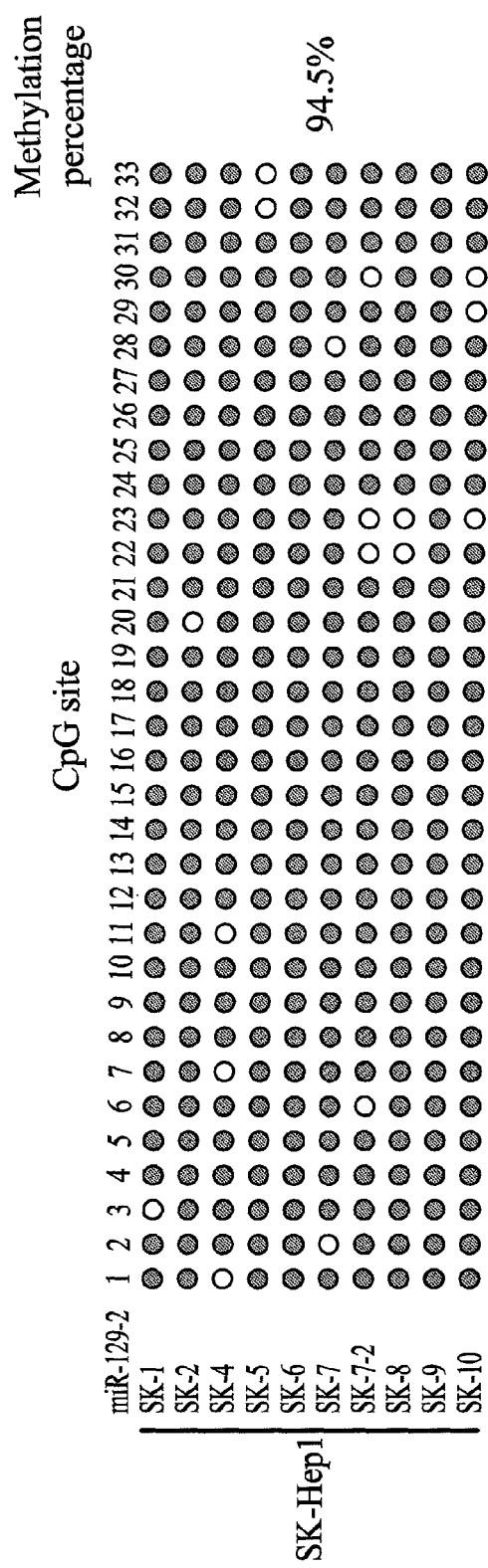

Bisulfite sequencing was used to further examine the methylation status of miR-129-2 in HCC and normal liver cells. In total, thirty three CpG sites were examined. In general, hypomethylation was observed in both of normal liver cell (HH) and tissue (FIGS. 2A~2B). The methylation percentage of miR-129-2 in normal liver tissues, NL-1663 and NL-4149, as well as normal liver cell HH was 2.1%, 3.3% and 0.6%, respectively. In contrast, the methylation percentage in HCC cells, HepG2, HuH7, J7, Hep3B, Mahlavu and SK-Hep1 was 64.5%, 58.8%, 71.5%, 79.7%, 72.7% and 94.5%, respectively (FIGS. 2C~2F). These results indicated that miR-129-2 hypermethylation was a frequent event in HCC cells compared with normal liver cells.

Example 2

DNA Methylation Regulating miR-129-2 Expression in HCC Cells

Figure 3A:
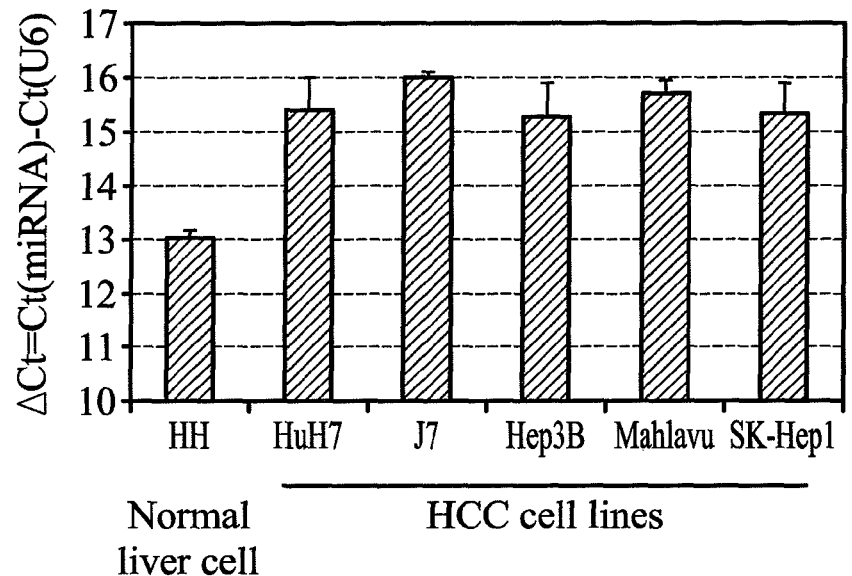
FIG. 3A shows the expression level of miR-129-2 in a normal liver cell (HH) and HCC cells according to the embodiment.
Figure 3B:
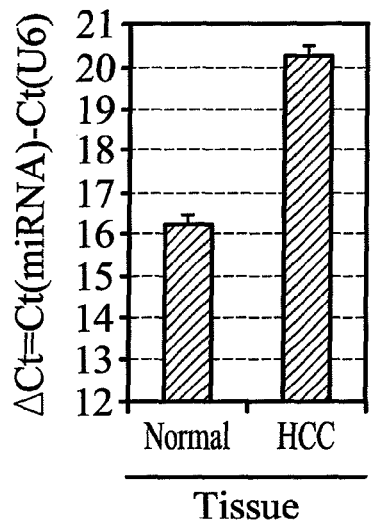
FIG. 3B shows the expression level of miR-129-2 in normal liver tissue and HCC tissue according to the embodiment.
Figure 3C:
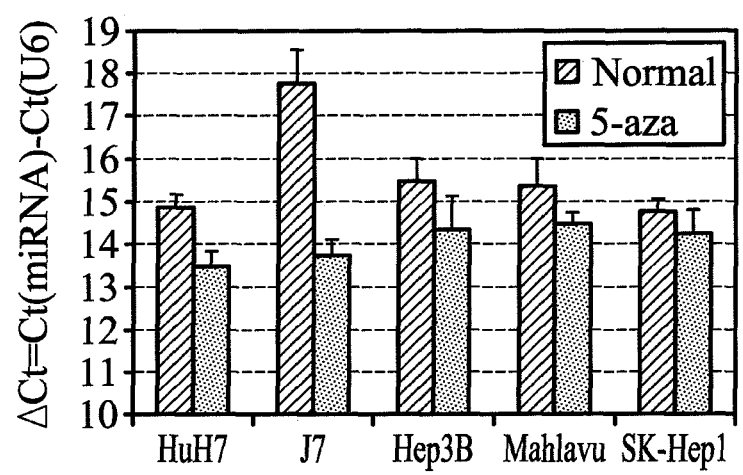
FIG. 3C shows the expression level of miR-129-2 with or without 5-aza-cytidine treatment in HCC cells according to the embodiment.

In order to evaluate whether miR-129-2 expression was regulated by DNA methylation, the expression level of miR-129-2 between normal liver cells and HCC cells was examined by quantitative reverse transcription PCR. The miR-129-2 expression was decreased in all of HCC cells compared with a normal liver cell, HH (FIG. 3A). Similarly, the miR-129-2 in HCC tissue sample showed 16-fold lower expression level than that in normal liver sample pool (FIG. 3B). Furthermore, after the treatment of 5-aza-cytidine, an inhibitor of DNA methyltransferase, the miR-129-2 expression level was significantly elevated by 2.5-fold in HuH7 cell and 16-fold in J7 cell compared with untreated cell (FIG. 3C). These results suggested that DNA methylation regulated the miR-129-2 expression and led to decreased expression of miR-129-2 in HCC cells.

Example 3

MiR-129-2 Functioned as a Tumor Suppressor miRNA in HCC

Figure 4A:
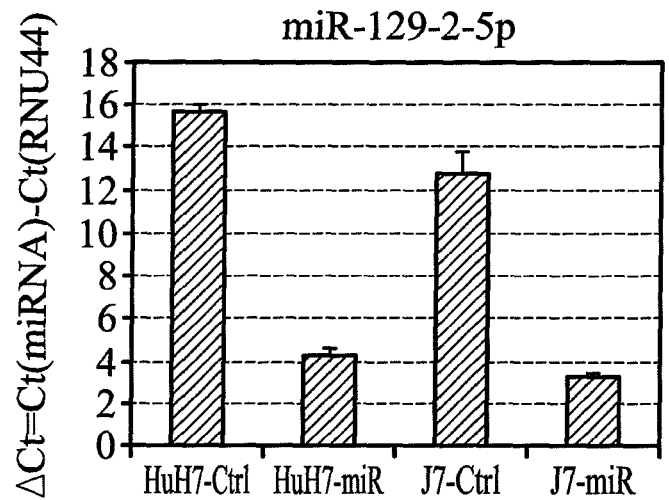
FIGS. 4A and 4B show the expression level of miR-129-2 in HuH7 and J7 cells with or without lenti-miR-129-2 infection according to the embodiment.
Figure 4B:
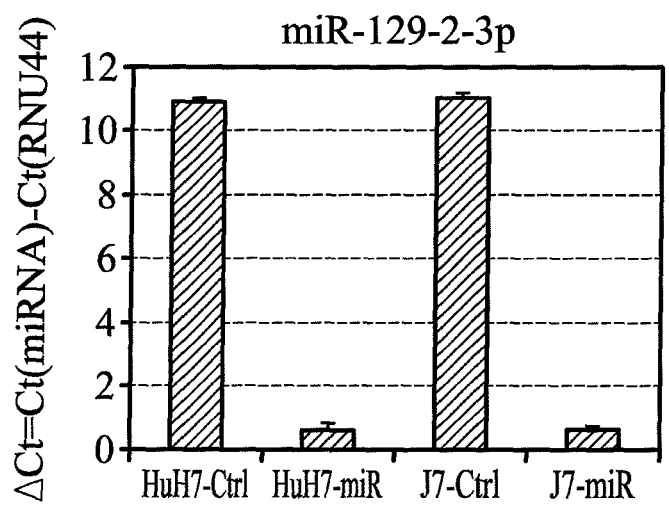
Figure 4C:
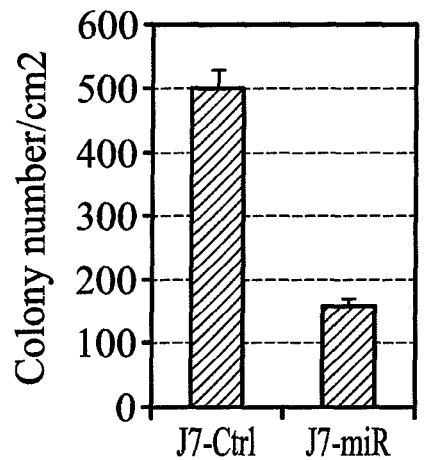
FIG. 4C shows the colony formation of J7 cells with or without lenti-miR-129-2 infection according to the embodiment.
Figure 4D:
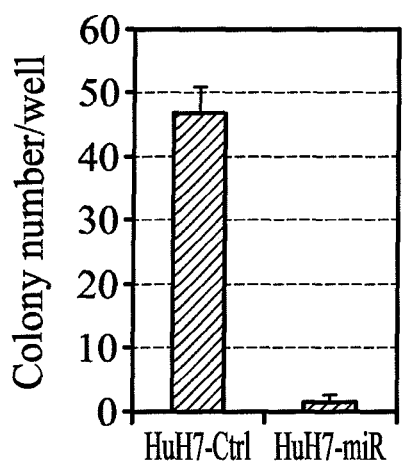
FIG. 4D shows the colony formation of HuH7 with or without lenti-miR-129-2 infection according to the embodiment.

To assess the function of miR-129-2 in HCC, first, we generated miR-129-2 expressing HCC cells by infection of lentivirus harboring miR-129-2 precursor (lenti-miR-129-2). We used Taqman assay to determine the expression of mature miR-129-2 in HCC cells infected by lenti-miR-129-2. In HuH7 cell, lenti-miR-129-2 infection led to miR-129-2-5p and miR-129-2-3p overexpression by about 2000-fold and 1000-fold, respectively, compared with control infection cell (FIGS. 4A~4B). Similarly, J7 cell infected by lenti-miR-129-2 showed about more than 500-fold miR-129-2-5p expression and 1000-fold miR-129-2 expression compared with controlled infection cell. We found that miR-129-2 possessed an ability to reduce the anchorage-independent growth of HCC cells. Only one third of the cell colonies were observed in J7 expressing miR-129-2 compared with control infection cell (FIG. 4C). In the same way, HuH7 infected by control lentivirus showed an average of 47 colonies per well (FIG. 4D). In contrast, nearly no colony can be detected in HuH7 expressing controlled miRNA. These results indicated that miR-129-2 may function as a tumor suppressor miRNA in HCC.

Example 4

MiR-129-2 Hypermethylation and Down-Regulation in HCC Clinical Samples

Figure 5A:
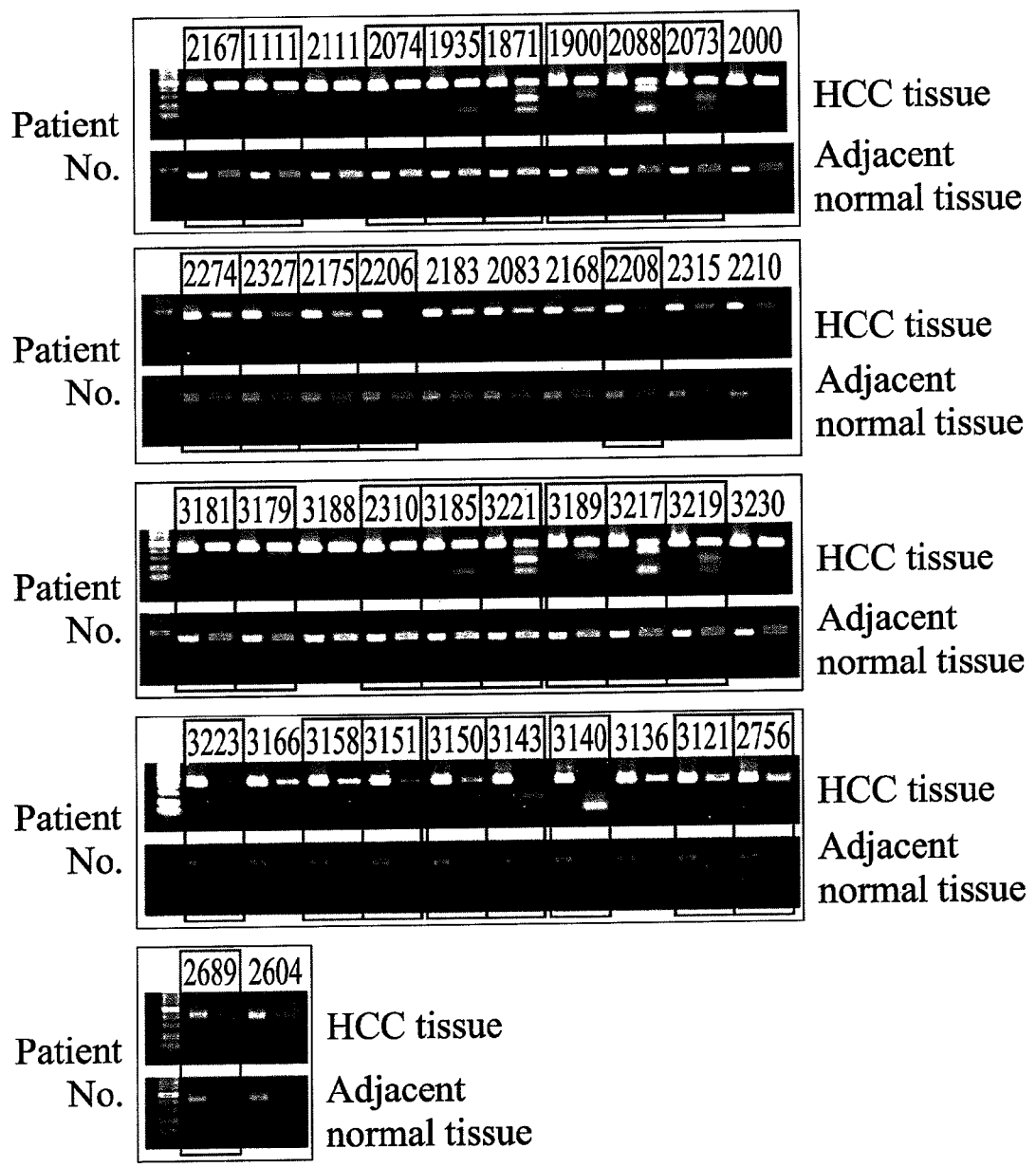
FIG. 5A shows the methylation status of miR-129-2 from tissue samples (42 pairs of HCC) by COBRA analysis according to the embodiment.
Figure 5B:
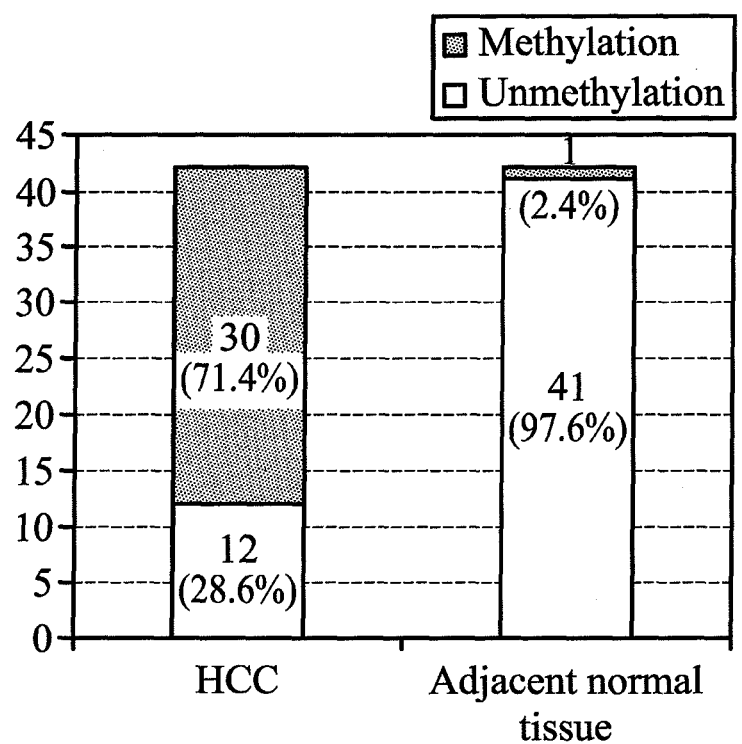
FIG. 5B shows the methylation percentage of miR-129-2 from tissue samples (42 pairs of HCC) according to COBRA analysis according to the embodiment.
Figure 5C:
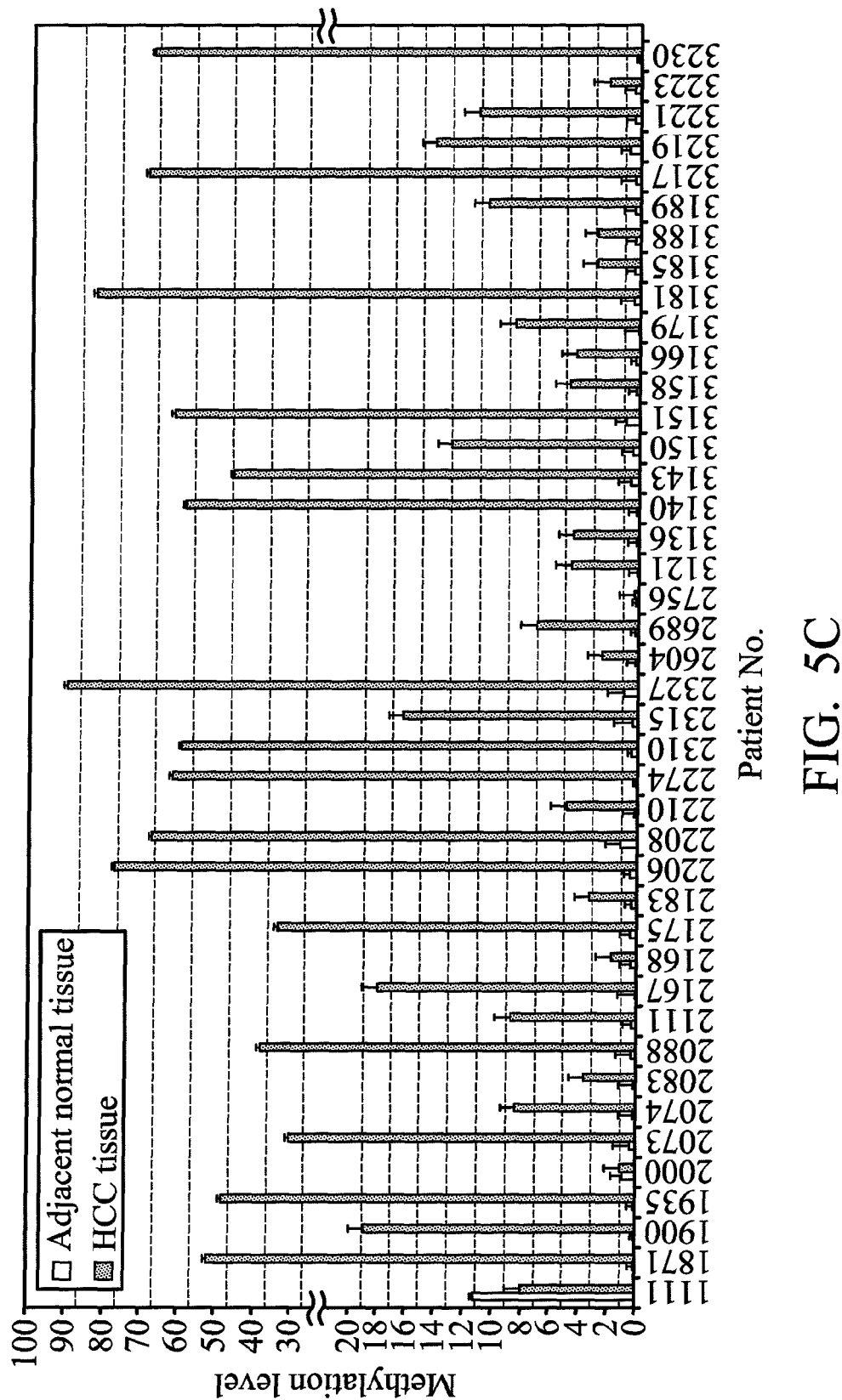
FIG. 5C shows methylation level of miR-129-2 from tissue samples by q-MSP method according to the embodiment.
Figure 5D:
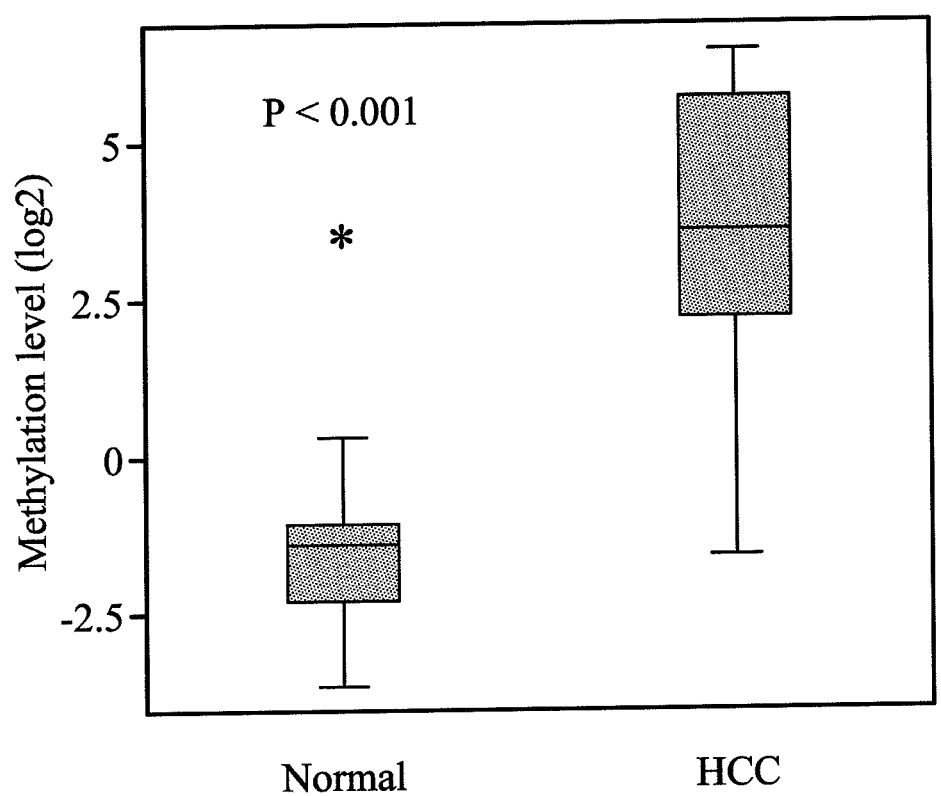
FIG. 5D shows a box plot of methylation level in HCC and adjacent normal tissues according to the embodiment.

To evaluate the methylation status of miR-129-2 in clinical samples, COBRA was used to analyze 42 pairs of HCC tumors and adjacent normal tissues (FIG. 5A). 30 out of 42 (~71%) HCC tissues showed miR-129-2 hypermethylation (FIG. 5B). By contrast, the miR-129-2 hypermethylation was only observed in one adjacent normal tissue. In order to further quantify the methylation level, quantitative methylation specific PCR was performed. Almost all of the clinical samples showed higher methylation level of miR-129-2 in HCC tissues compared with the adjacent normal tissues except for three cases (patient No. 1111, 2000 and 2756) (FIGS. 5C~5D). In addition, the results of q-MSP were significantly correlated with those of COBRA. These results showed that miR-129-2 was hypermethylated in HCC clinical samples, corresponded with the results in HCC cells.

Figure 6A:
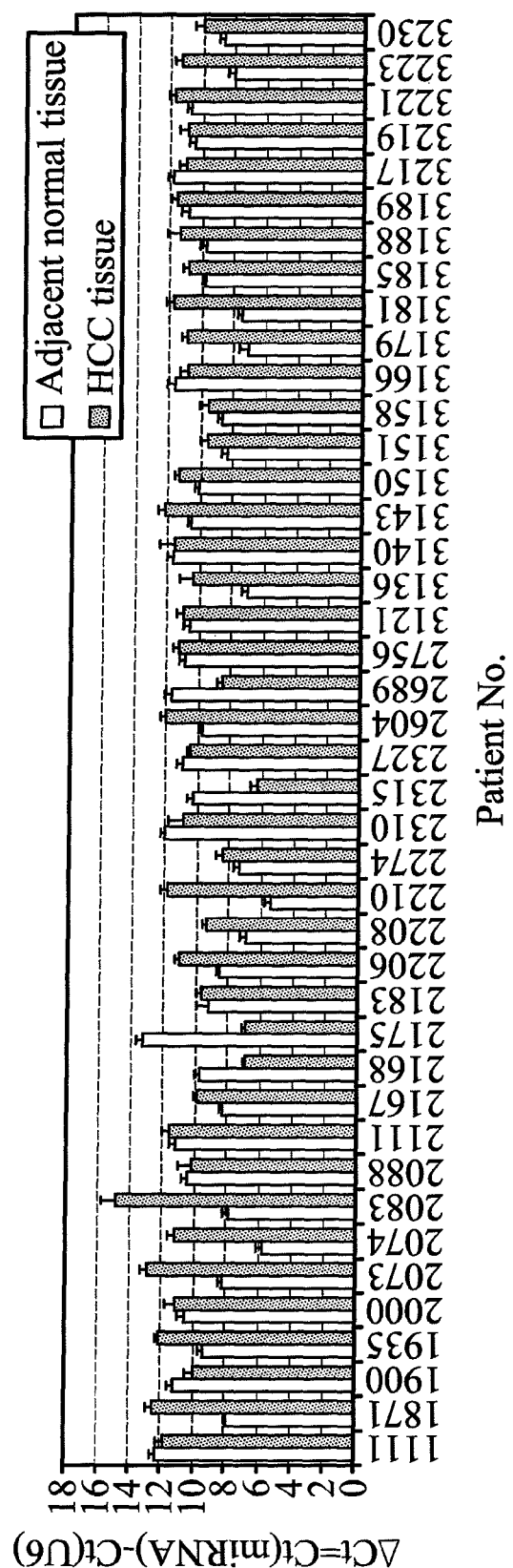
FIG. 6A shows the expression level of miR-129-2 from tissue samples by qRT-PCR method according to the embodiment.
Figure 6B:
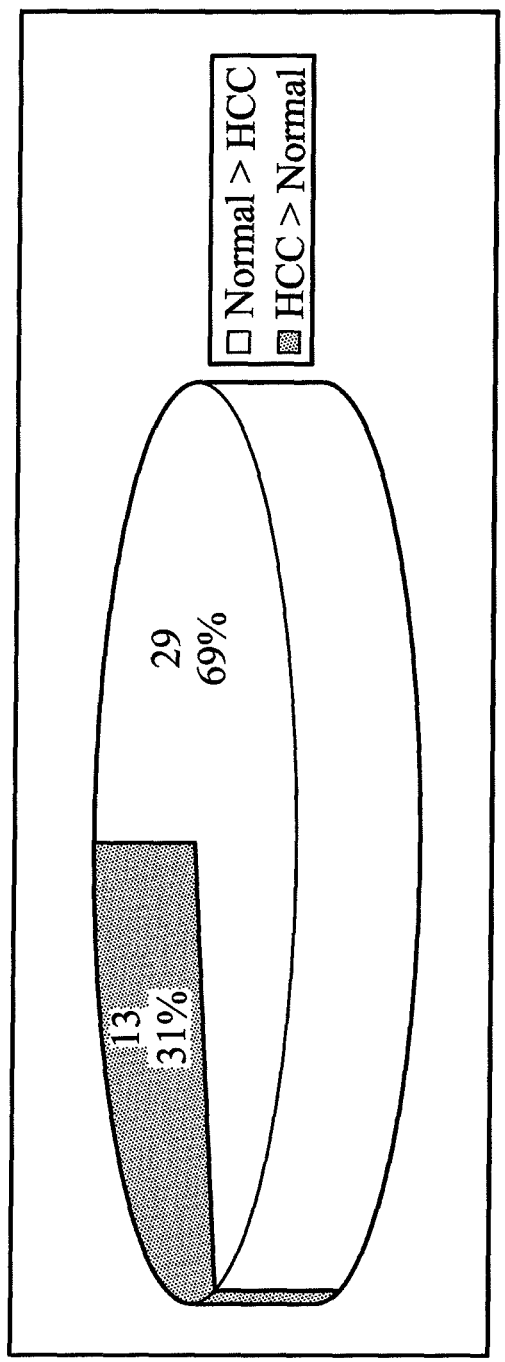
FIG. 6B shows the percentage of the expression of miR-129-2 in the HCC tissues and adjacent normal tissues according to the embodiment.

Furthermore, to determine whether the expression of miR-129-2 was down-regulated by DNA methylation, qRT-PCR was performed. In 42 HCC clinical samples, the expression of miR-129-2 was repressed in 29 (~69%) HCC samples compared with the adjacent normal tissues (FIGS. 6A~6B).

These results showed that miR-129-2 was hypermethylated and down-regulated in HCC samples but not in adjacent normal tissues, indicating that the differential expression and/or the methylation level of miR-129-2 maybe can act as a marker for HCC diagnosis.

Example 5

Methylation Level of miR-129-2 in HCC Plasma Samples

Figure 7A:
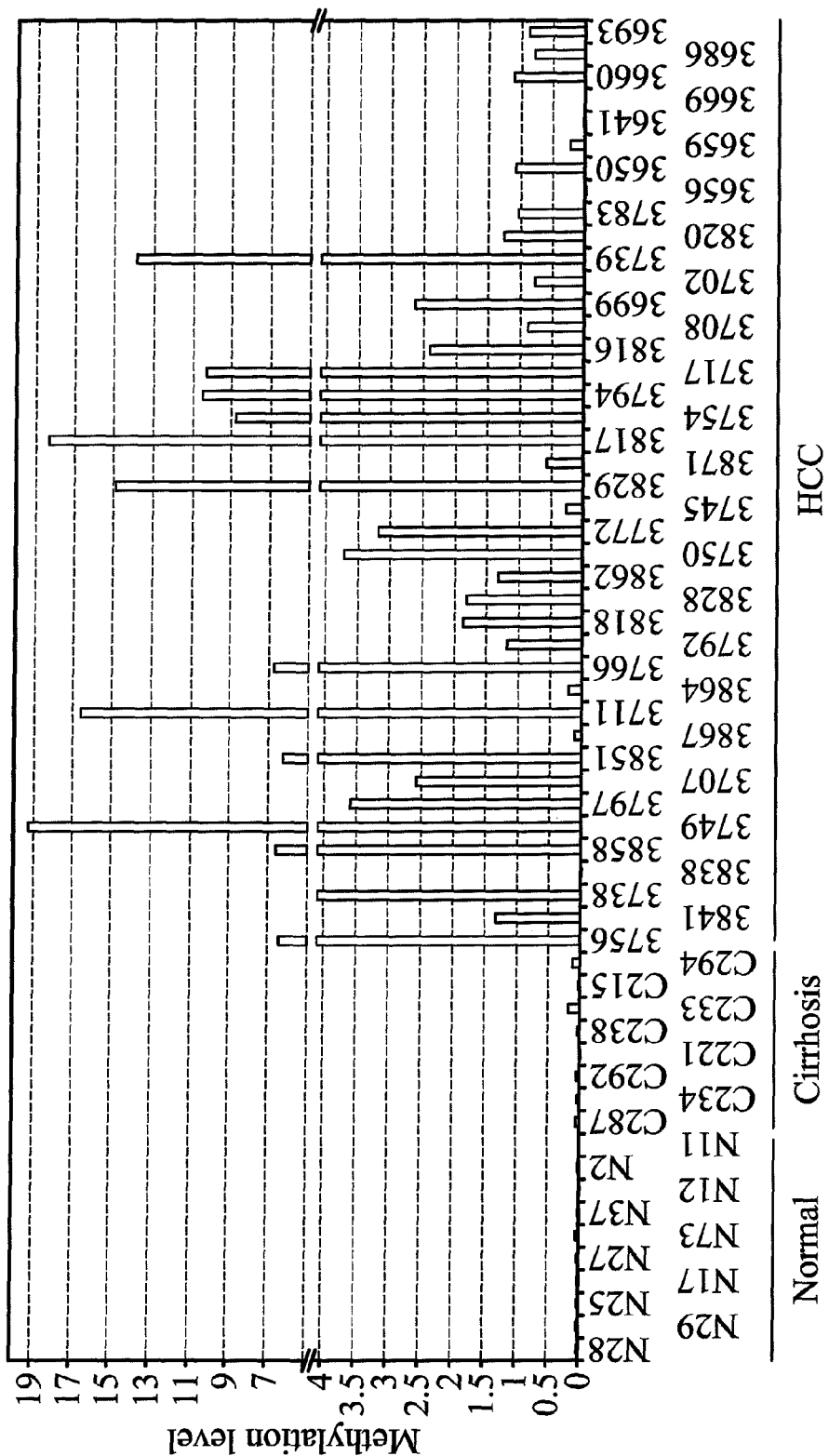
FIG. 7A shows methylation level of miR-129-2 in HCC plasma, cirrhotic plasma and healthy plasma by q-MSP method according to the embodiment.
Figure 7B:
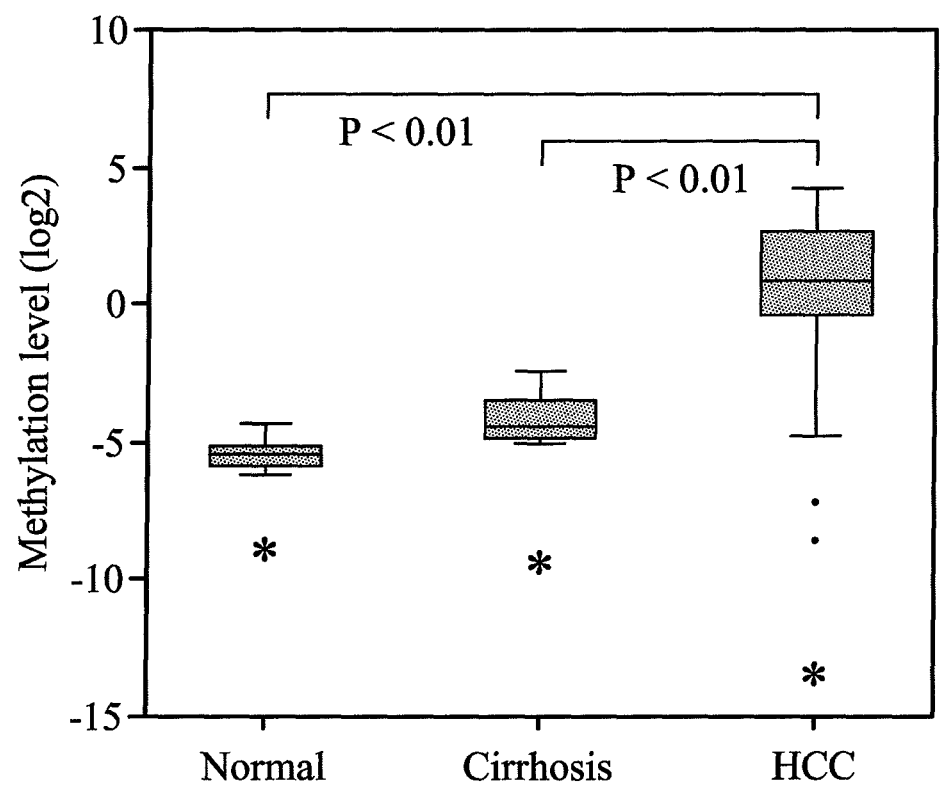
FIG. 7B shows box plot of methylation level in HCC plasma, cirrhotic plasma and normal plasma samples according to the embodiment.
Figure 7C:
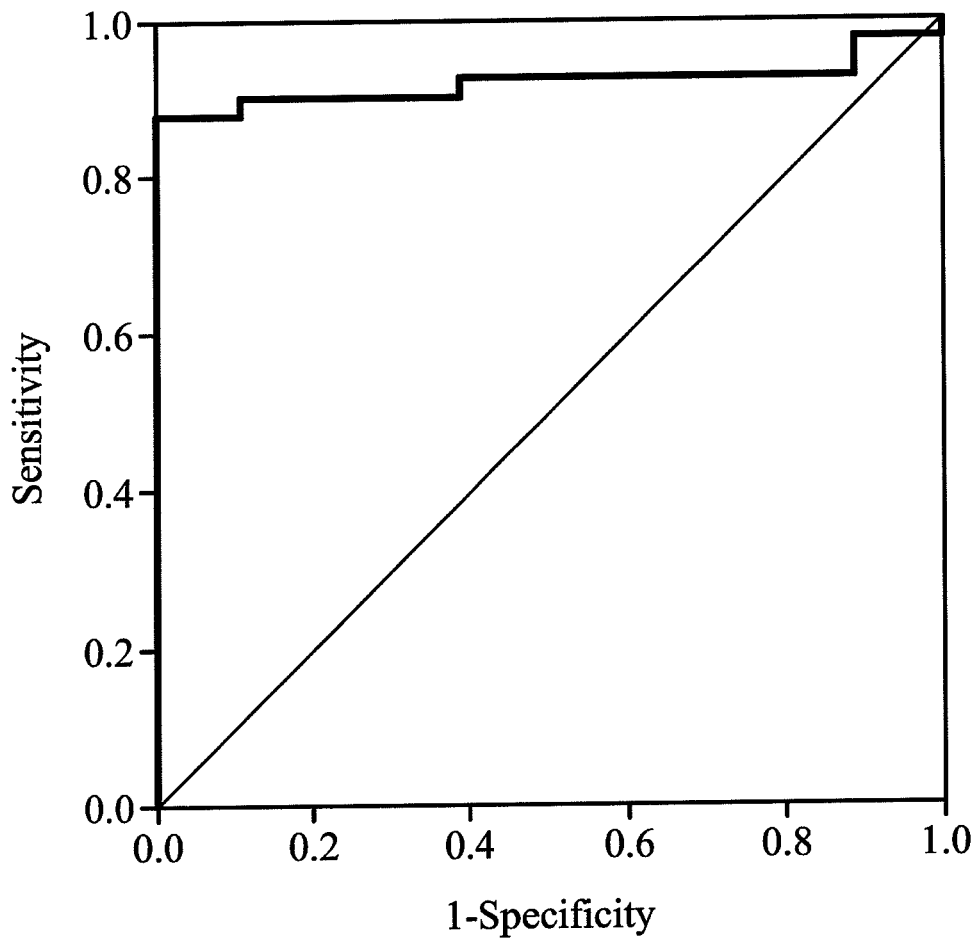
FIG. 7C shows ROC curve for calculating the sensitivity and specificity of miR-129-2 methylation level between two groups; one containing HCC plasma sample, while the other comprised of healthy and cirrhotic plasma samples according to the embodiment.

Forty-one HCC plasma samples, eight cirrhotic plasma samples and ten healthy plasma samples were obtained from Chi Mei medical center, Tainan, Taiwan. The samples were undergone q-MSP for determining the methylation level of miR-129-2. The methylation level was more than 0.1 in 37 (90%) of 41 HCC plasma samples (FIG. 7A). By contrast, none of healthy donor can be detected in plasma samples with more than 0.05 of methylation level, and only 2 cirrhotic plasma samples showed more than 0.1 (FIG. 7A). For further statistical analysis, the methylation level was transformed into log 2 value. Statistical analysis showed that HCC plasma had significantly higher miR-129-2 methylation level than healthy or cirrhotic plasma (P<0.01) (FIG. 7B). Sensitivity, specificity, AUC (area under the curve) and cutoff value of miR-129-2 methylation level was determined using ROC (receiver operating characteristic curve) analysis. At a cut-off value of −2.36, it was able to distinguish HCC from healthy and cirrhosis with sensitivity and specificity of 88% and 100%, respectively (AUC=0.92, SE=0.039, 95% CI=0.843-0.997, P<0.001) (FIG. 7C). ROC curve analysis revealed a high accuracy of using miR-129-2 methylation in HCC diagnosis.

It will be apparent to those skilled in the art that various modifications and variations can be made to the disclosed embodiments. It is intended that the specification and examples be considered as exemplary only, with a true scope of the disclosure being indicated by the following claims and their equivalents.

---

What is claimed is:

1. A method for diagnosing liver cancer in a human subject, comprising:
    obtaining a bio-sample from the subject, wherein the bio-sample is liver tissue, blood, serum, or plasma;
    detecting a methylation level of one or more CpG sites of the miR-129-2 gene in the bio-sample, wherein said detecting is performed by a method selected from: combined bisulfate restriction analysis (COBRA) using a primer pair as set forth in SEQ ID NOs: 4 and 5; and quantitative methylation-specific PCR (q-MSP) using a primer pair as set forth in SEQ ID NOs: 8 and 9;
    comparing the methylation level of the one or more CpG sites of the miR-129-2 gene in the bio-sample with a methylation level of the same CpG sites from a control subject that does not have liver cancer, wherein the methylation level of the CpG sites in the bio-sample from the subject is higher than the methylation level of the CpG sites in the control; and
    correlating the methylation level of the CpG sites in the bio-sample with a diagnosis of liver cancer in the subject.

2. The method as claimed in claim 1, wherein the miR-129-2 gene comprises the nucleotide sequence as set forth in SEQ ID NO: 1.

3. The method as claimed in claim 1, wherein the bio-sample is obtained from frozen liver tissue, blood, serum, or plasma.

4. The method as claimed in claim 1, wherein the bio-sample is obtained from liver tissue, blood, serum, or plasma that has not been frozen.

* * * * *

SEQUENCE LISTING

```
<160> NUMBER OF SEQ ID NOS: 9

<210> SEQ ID NO 1
<211> LENGTH: 90
<212> TYPE: DNA
<213> ORGANISM: Homo sapiens
<220> FEATURE:
<221> NAME/KEY: Precursor_RNA
<223> OTHER INFORMATION: miR-129-2

<400> SEQUENCE: 1 tgccctctcgc gaatcttttt gcggtctggg cttgctgtac ataactcaat agccggaagc     60
ccttacccca aaaagcattt gcggagggcg                                      90

<210> SEQ ID NO 2
<211> LENGTH: 22
<212> TYPE: DNA
<213> ORGANISM: Homo sapiens
<220> FEATURE:
<221> NAME/KEY: mat_peptide
<223> OTHER INFORMATION: miR-129-2-5p

<400> SEQUENCE: 2 vcttttttgcg gtctgggctt gc                                             22

<210> SEQ ID NO 3
<211> LENGTH: 22
<212> TYPE: DNA
<213> ORGANISM: Homo sapiens
<220> FEATURE:
<221> NAME/KEY: mat_peptide
<223> OTHER INFORMATION: miR-129-2-3p
```

```
<400> SEQUENCE: 3
aagcccttac cccaaaaagc at                                          22

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide for miR-129-2

<400> SEQUENCE: 4
gttggggaga tttagtttgt t                                           21

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide for miR-129-2

<400> SEQUENCE: 5
cctactccaa ttccccctat aatac                                       25

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide for miR-129-2

<400> SEQUENCE: 6
gcgaatcttt ttgcggtct                                              19

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide for miR-129-2

<400> SEQUENCE: 7
ccgtcttctc gacgagtgc                                              19

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide for miR-129-2

<400> SEQUENCE: 8
ttagtttgtt cggttttagg gttc                                        24

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide for miR-129-2

<400> SEQUENCE: 9 acttttaaa ataaaaactt ccgac                                        25
```